US00PP29576P3

(12) United States Plant Patent
Koie et al.

(10) Patent No.: US PP29,576 P3
(45) Date of Patent: Aug. 7, 2018

(54) HOP PLANT NAMED 'FURANO 0902D GO'

(50) Latin Name: ***Humulus lupulus* L.**
Varietal Denomination: Furano 0902D go

(71) Applicant: Sapporo Breweries Limited, Tokyo (JP)

(72) Inventors: Koichiro Koie, Hokkaido (JP); Narushi Suda, Hokkaido (JP); Yutaka Itoga, Hokkaido (JP); Mitsuhiro Uemoto, Hokkaido (JP); Yasunori Arai, Hokkaido (JP); Masanobu Goto, Hokkaido (JP)

(73) Assignee: Sapporo Breweries Limited, Tokyo (JP)

( * ) Notice: Subject to any disclaimer, the term of this patent is extended or adjusted under 35 U.S.C. 154(b) by 22 days.

(21) Appl. No.: 14/757,380

(22) Filed: Dec. 21, 2015

(65) Prior Publication Data

US 2016/0192560 P1 Jun. 30, 2016

(30) Foreign Application Priority Data

Dec. 24, 2014 (JP) ..... PBR 29813

(51) Int. Cl.
*A01H 5/02* (2018.01)

(52) U.S. Cl.
USPC ..... Plt./236
CPC ..... *A01H 5/02* (2013.01)

(58) Field of Classification Search
USPC ..... Plt./236
CPC ..... A01H 5/02
See application file for complete search history.

*Primary Examiner* — Kent L Bell
(74) *Attorney, Agent, or Firm* — James M. Weatherly; Bethany R. Roahrig; Cochran Freund & Young LLC

(57) ABSTRACT

A new hop plant particularly distinguished by having a cylindrical plant shape, alpha acid content of 13.4% in dry matter, a ratio content of beta to alpha of 0.6, a content of cohumulone to alpha acids of 32%, and a flowery and fruity flavor, is disclosed.

2 Drawing Sheets

Genus and species: *Humulus lupulus* L.
Variety denomination: 'Furano 0902D go'.

CROSS REFERENCE TO RELATED APPLICATION

The present application claims priority to Japan Plant Variety Protection Application No. 29813, as filed on Dec. 24, 2014, the entire contents are herein incorporated by reference for all the application teaches and discloses.

BACKGROUND OF THE NEW PLANT

The present invention comprises a new and distinct variety of hop, botanically known as *Humulus lupulus* L. and hereinafter referred to by the variety name 'Furano 0902D go'. 'Furano 0902D go' is a selection from a controlled cross-pollination of the proprietary hop female parent '990340' and the proprietary male parent '000210'.

The proprietary female hop line '990340' and the proprietary hop line '000210' were cross-pollinated in Kamifurano, Hokkaido, Japan and seeds were obtained. The seeds were sown and plants were grown for evaluation. A plant line was selected in March of 2009 in Kamifurano, Hokkaido, Japan and named 'Furano 0902D go'. In 2009, 'Furano 0902D go' was first vegetatively propagated by in Kamifurano, Hokkaido, Japan via vegetative cuttings. 'Furano 0902D go' was found to reproduce true to type in successive generations of asexual propagation via vegetative cuttings in Kamifurano, Hokkaido, Japan.

SUMMARY

The following are the most outstanding and distinguishing characteristics of this new variety when grown under normal horticultural practices in Kamifurano, Hokkaido, Japan.

1. Cylindrical plant shape;
2. Alpha acid content of 13.4% in dry matter;
3. Ratio content of beta to alpha of 0.6;
4. Content of cohumulone to alpha acids of 32%; and
5. A flowery and fruity flavor.

DESCRIPTION OF THE PHOTOGRAPHS

This hop plant is illustrated by the accompanying photographs which show the plant's overall plant shape, leaf shape and cone shape. The photographs are of six-year-old plants grown in Kamifurano, Hokkaido, Japan in August 2014. The colors shown are as true as can be reasonably obtained by conventional photographic procedures.

DESCRIPTION OF THE NEW VARIETY

Figure 1:
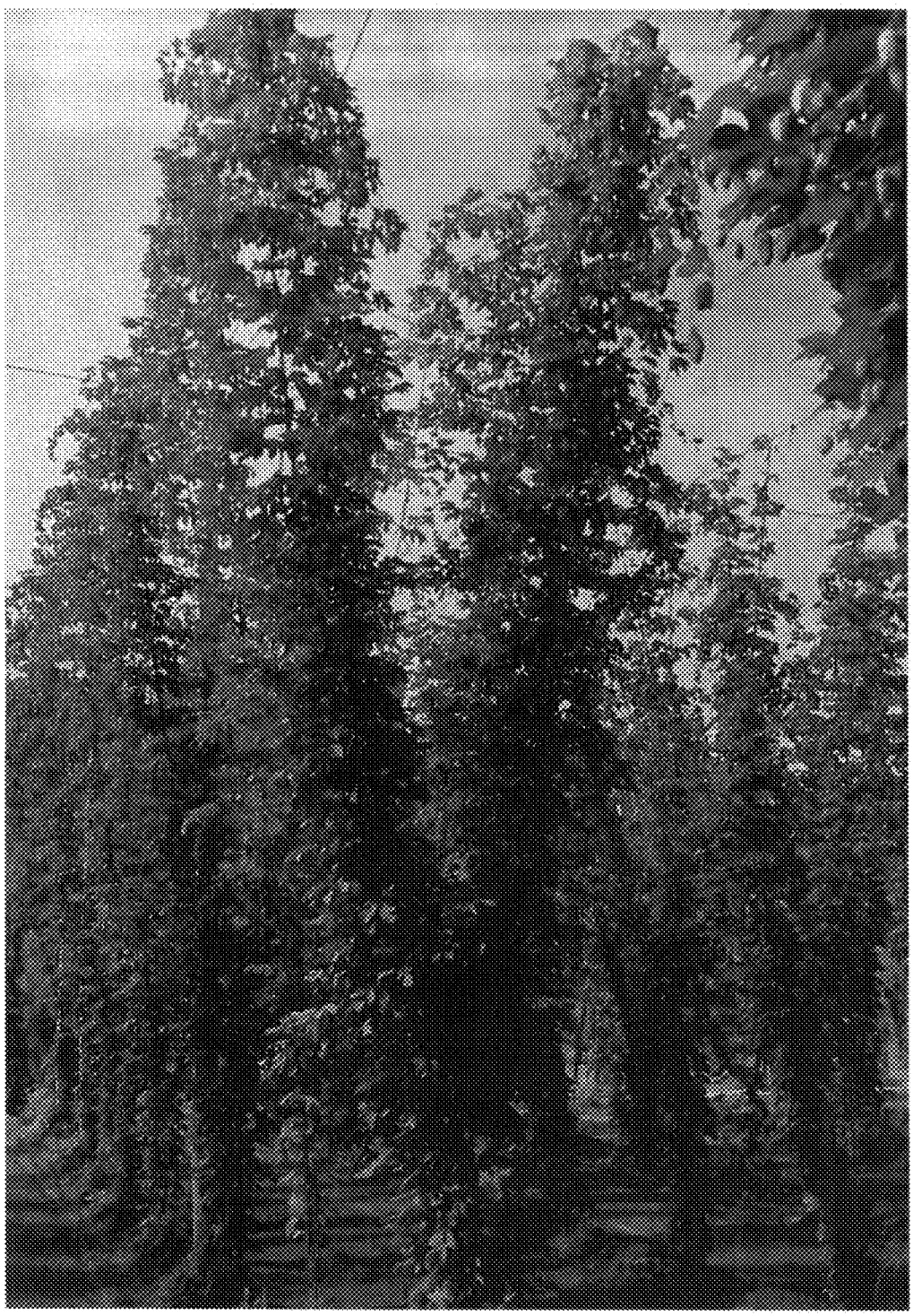
FIG. 1 shows the plant shape of 'Furano 0902D go'.
Figure 2:
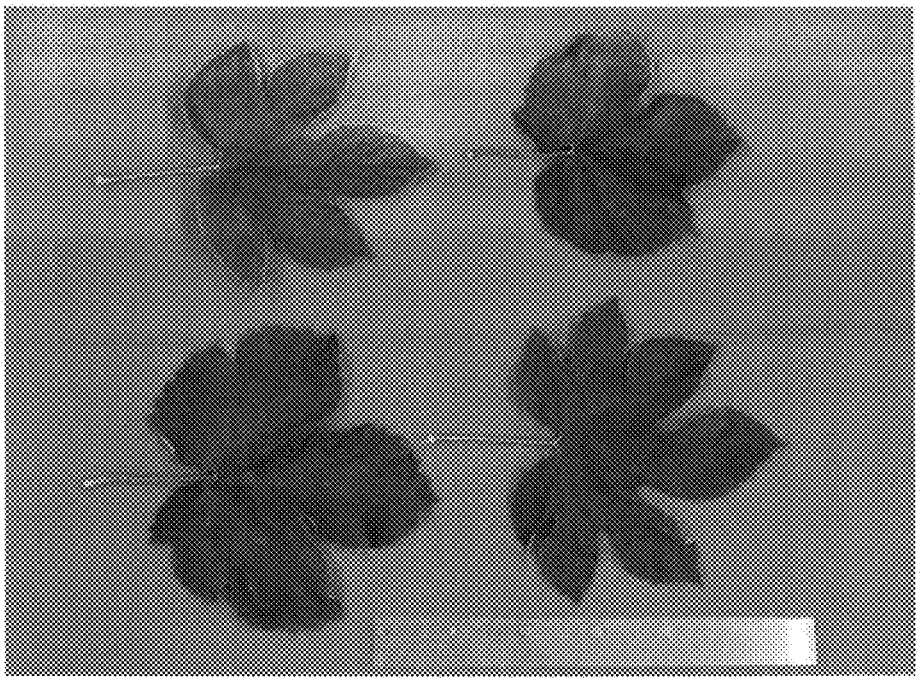
FIG. 2 shows the leaf shape of 'Furano 0902D go' and three commercial hops varieties in Japan. The lower right shows 'Furano 0902D go', the upper right shows 'Little Star', the upper left shows 'Shinsyu Wase', and the lower left shows 'Furano Special'.
Figure 3:
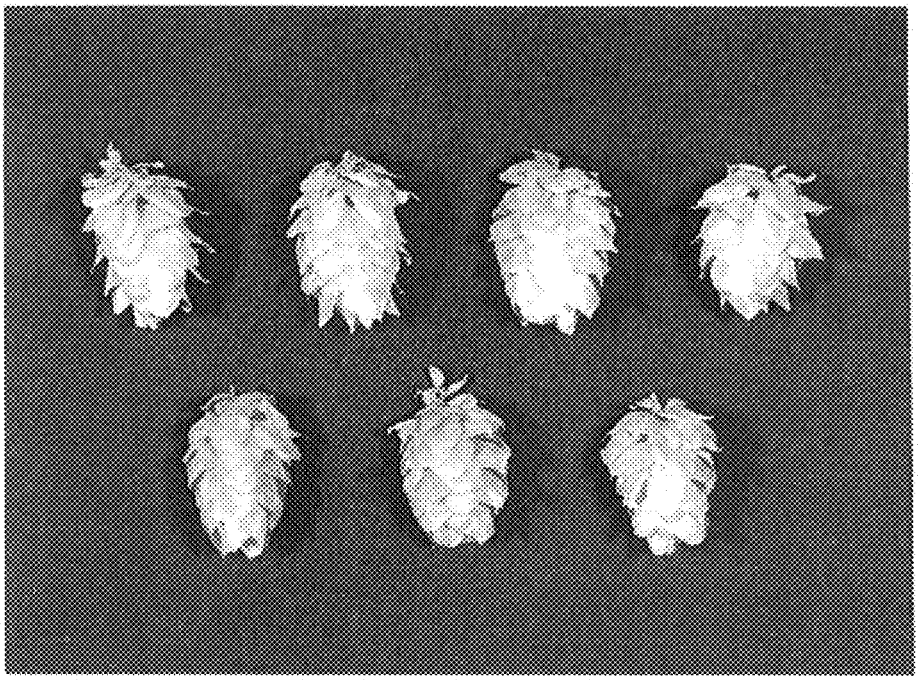
FIG. 3 shows the cone shape of 'Furano 0902D go'.

The following detailed descriptions set forth the distinctive characteristics of 'Furano 0902D go'. The data, which define these characteristics, were collected from asexual reproductions carried out in Kamifurano, Hokkaido, Japan. Data was collected on five- and six-year-old plants in Kamifurano, Hokkaido, Japan during the 2013 to 2017 growing seasons. Color references are to Japan Horticultural Plant Color Chart (1987, Japan Color Research Institute).

Classification:

*Family*.—Cannabaceae.

*Classification*.—*Humulus lupulus* L.

*Common name*.—Hop.

Propagation:

*Type*.—Vegetative cuttings.

Plant description:

*Plant and growth habit*.—The plant growth type is normal, not dwarf.

*Plant height*.—5.5 m when grown on a trellis.

*Plant diameter*.—1.2 m to 1.5 m.

*Plant shape*.—Cylindrical.

Lateral branch description:

*Length*.—Average is 0.82 m.

*Diameter*.—Average is 3.4 mm; ranges between 2.8 mm and 4.0 mm.

*Internode length*.—Average is 17.6 cm; ranges between 10.0 cm and 24.0 cm on the lateral branch at the middle of the plant.

*Color*.—The color of the ridge line is a deep reddish purple (Japan Color Chart No. 8907); the color of the area in-between is a soft yellow green (Japan Color Chart No. 3511).

Foliage description:

*Arrangement*.—Opposite.

*Shape*.—7 lobes; sometimes the middle lobe is additionally lobed in 3.

*Length*.—Average is 18.4 cm; ranges between 15.0 cm and 23.0 cm.

*Width*.—Average is 22.1 cm (measured in 2016); ranges between 19.0 cm and 25.0 cm.

*Color*.—Upper surface, Dark Green (Japan Color Chart No. 3707).

*Apex*.—Accuminate.

*Margin*.—Serrate to spiny.

*Base*.—Auriculate.

*Venation pattern*.—Palmate.

*Venation color*.—Dark green (Japan Color Chart No. 3707).

*Blistering*.—Upper surface: Medium.

*Petiole*.—Length: Average is 8.8 cm; ranges between 7.5 cm and 10.0 cm. Diameter: Average is 3.7 mm; ranges between 2.9 mm and 4.2 mm measured in the middle. Color: From base to bine is a dark red (Japan Color Chart No. 0410).

Inflorescence buds:

*Cone size*.—Medium; average length is 28.7 mm; ranges between 24.0 mm and 33.0 mm and average diameter is 21.6 mm; ranges between 19.5 mm and 24.5 mm.

*Cone shape*.—Medium, ovate.

*A hundred cone weight*.—Light (15.2 g in dry matter).

*Color*.—Vivid yellow green (Japan Color Chart No. 3311).

*Lupulin glands*.—Number per cone: Normal. Shape: Round. Color: Bright yellow (Japan Color Chart No. 2506).

*Flowering date* (*the date when half of the plants being in bloom*).—July 16$^{th}$.

*Harvest date*.—August 30th.

Bracts:

*Shape*.—Aristate.

*Length*.—Average is 17.2 mm; ranges between 14.0 cm and 19.0 cm.

*Width*.—Average is 11.0 mm; ranges between 9.0 cm and 13.0 cm.

*Margin*.—Entire.

*Color*.—Dull yellow green (Japan Color Chart No. 3110).

Bracteoles:

*Shape*.—Oval.

*Length*.—Average is 12.0 mm; ranges between 10.5 mm and 13.5 mm.

*Width*.—Average is 7.4 mm; ranges between 6.0 mm and 8.0 mm.

*Apex*.—Round.

*Margin*.—Entire.

*Color*.—Light yellow green (Japan Color Chart No. 3503).

Bines:

*Length*.—Greater than 5.5 m.

*Diameter*.—Average is 8.7 mm; ranges between 7.0 mm and 10.5 mm.

*Internode length*.—Average is 28.0 cm; ranges between 24.0 cm and 34.0 cm.

*Color*.—The color of the ridge line is deep reddish purple (Japan Color Chart No. 8907) and the color of the area in-between is soft yellow green (Japan Color Chart No. 3511).

*Anthocyanin coloration*.—Medium.

*Stipule number per bine*.—Equal to double the number of internodes.

*Stipule direction*.—Upper.

*Stipule color*.—Light yellow green (Japan Color Chart No. 3304).

Pedicels: Not observed.

Reproductive organs:

*Stamens*.—Not observed.

*Pistils*.—Not observed.

Yield: 1.64 tons/hectare (2014 to 2016 average).

Disease and pest/insect resistance: None observed.

*Brewing characteristics*.—Content of alpha acid is 13.4% in dry matter. Content of beta acids is 5.9% (data from 2013). Ratio content of beta to alpha is 0.6. Content of humulene is 2.7% (data from 2015). Content of caryophyllene is 9.8% (data from 2015). Ratio content of humulene to caryophyllene is 0.13 (data from 2015). Content of cohumulone to alpha acids is 32%. Content of myrcene is 62.0% (data from 2015). Content of farnesene is 21.2% (data from 2015). Content of linalool is 1.3% (data from 2015). Total oil: 1.80 mL per 100 g of cone weight Flavor of 'Furano 0902D go' is flowery and fruity. Storage stability: 56.5% after 6 months at room temperature (data from 2015).

COMPARISON WITH PARENTAL LINES AND KNOWN VARIETY

'Furano 0902D go' is a distinct variety of hop. 'Furano 0902D go' is distinguished from its female parent '990340' as described in Table 1:

TABLE 1

| Comparison with Parental Lines | | |
|---|---|---|
| Characteristic | Variety 'Furano 0902D go' | Female parent '990340' |
| Flowering date | 16th of July | 15th of July |
| Harvest date | 30th of August | 29th of August |
| Content of alpha acid in dry matter | 13.4% | 11.3% |
| Content of cohumulone in alpha acid | 32% | 25% |

'Furano 0902D go' is distinguished from its male parent '000210' in that 'Furano 0902D go' develops female flowers that develop into mature hop cones without producing pollen, whereas '000210' produces pollen without developing into female flowers.

'Furano 0902D go' is distinguished from the commercial hop variety 'Little Star' (not patented). Differences between the two varieties are described in Table 2:

TABLE 2

| Comparison with Similar Variety | | |
|---|---|---|
| Characteristic | Variety 'Furano 0902D go' | Commercial line 'Little Star' |
| Flowering date | 16th of July | 7th of July |
| Harvest date | 30th August | 21st August |
| Content of alpha acid in dry matter | 13.4% | 7.3% |
| Ratio content of beta acid to alpha acid | 0.6 | 0.7 |
| Content of cohumulone in alpha acid | 32% | 22% |

We claim:

1. A new and distinct variety of hop plant named 'Furano 0902D go' as illustrated and described herein.

* * * * *